US011013494B2

(12) United States Patent
Lee et al.

(10) Patent No.: US 11,013,494 B2
(45) Date of Patent: May 25, 2021

(54) ULTRASOUND IMAGING APPARATUS AND ULTRASOUND IMAGE DISPLAY METHOD

(71) Applicant: SAMSUNG MEDISON CO., LTD., Hongcheon-gun (KR)

(72) Inventors: Jung-eun Lee, Hongcheon-gun (KR); Dong-kuk Shin, Hongcheon-gun (KR); Dal-kwon Koh, Hongcheon-gun (KR); Gil-ju Jin, Hongcheon-gun (KR); Soo-young Oh, Seoul (KR); Han-sung Hwang, Seoul (KR)

(73) Assignee: SAMSUNG MEDISON CO., LTD., Hongcheon-gun (KR)

(*) Notice: Subject to any disclaimer, the term of this patent is extended or adjusted under 35 U.S.C. 154(b) by 416 days.

(21) Appl. No.: 15/698,890

(22) Filed: Sep. 8, 2017

(65) Prior Publication Data
US 2018/0199919 A1    Jul. 19, 2018

(30) Foreign Application Priority Data

Jan. 18, 2017  (KR) .................. 10-2017-0008684

(51) Int. Cl.
*A61B 8/08*  (2006.01)
*A61B 8/00*  (2006.01)
*G16H 50/30*  (2018.01)

(52) U.S. Cl.
CPC ............. *A61B 8/485* (2013.01); *A61B 8/085* (2013.01); *A61B 8/4405* (2013.01);
(Continued)

(58) Field of Classification Search
CPC ....... A61B 8/485; A61B 8/4427; A61B 8/469; A61B 8/463; A61B 8/085; A61B 8/4405;
(Continued)

(56) References Cited

U.S. PATENT DOCUMENTS 6,413,218 B1   7/2002   Allison et al.
9,047,394 B2   6/2015   Hyun
(Continued)

FOREIGN PATENT DOCUMENTS

JP   2015226836 A   12/2015
KR   100803328 B1   2/2008
(Continued)

OTHER PUBLICATIONS

Wu, Min, R. F. Fraser, and Chang Wen Chen. "A novel algorithm for computer-assisted measurement of cervical length from transvaginal ultrasound images." IEEE Transactions on Information Technology in Biomedicine 8.3 (2004): 333-342 (Year: 2004).*
(Continued)

*Primary Examiner* — Pascal M Bui Pho
*Assistant Examiner* — Sean D Mattson
(74) *Attorney, Agent, or Firm* — Sughrue Mion, PLLC

(57) ABSTRACT

An ultrasound imaging apparatus includes a processor configured to set an internal orifice of an uterus (IOS) point indicating the IOS of a cervix and an external orifice of an uterus (EOS) point indicating the EOS of the cervix, from a cervix line indicating a cervical canal, set a region of interest (ROI) of the IOS and a ROI of the EOS based on the IOS point and the EOS point, and calculate degrees of elasticity in the ROI of the IOS and the ROI of the EOS, and a display configured to display information indicating the degrees of elasticity in the ROI of the IOS and the ROI of the EOS.

15 Claims, 11 Drawing Sheets

(52) U.S. Cl.
CPC ............ *A61B 8/4427* (2013.01); *A61B 8/463* (2013.01); *A61B 8/469* (2013.01); *A61B 8/5223* (2013.01); *G16H 50/30* (2018.01); *A61B 8/0866* (2013.01); *A61B 8/4477* (2013.01)

(58) Field of Classification Search
CPC .... A61B 8/4477; A61B 8/0866; A61B 8/5223
See application file for complete search history.

(56) References Cited

U.S. PATENT DOCUMENTS

| | | | |
|---|---|---|---|
| 2012/0014588 A1* | 1/2012 | Chono | A61B 8/00 382/133 |
| 2012/0232394 A1 | 9/2012 | Toji | |
| 2013/0158406 A1 | 6/2013 | Kabakov et al. | |
| 2014/0029815 A1 | 1/2014 | Kadir et al. | |
| 2014/0354776 A1 | 12/2014 | Kim et al. | |
| 2015/0141822 A1* | 5/2015 | Miyauchi | G06T 7/0012 600/438 |
| 2015/0265247 A1* | 9/2015 | Roh | A61B 8/488 600/438 |
| 2016/0040024 A1 | 2/2016 | Weingart et al. | |
| 2016/0166233 A1 | 6/2016 | Yoo et al. | |

FOREIGN PATENT DOCUMENTS

| | | |
|---|---|---|
| KR | 10-1194293 B1 | 10/2012 |
| KR | 101208216 B1 | 12/2012 |
| KR | 1020140140712 A | 12/2014 |
| KR | 10-1614373 B1 | 4/2016 |
| KR | 10-2016-0073168 A | 6/2016 |
| WO | 2012/148188 A2 | 11/2012 |
| WO | 2015/149805 A1 | 10/2015 |
| WO | 2016/040024 A1 | 3/2016 |

OTHER PUBLICATIONS

Swiatkowska-Freund, M., and K.Preis. "Elastography of the uterine cervix: implications for success of induction of labor." Ultrasound in Obstetrics & Gynecology 38.1 (2011): 52-56. (Year: 2011).*
Iams, Jay D. "Prediction and early detection of preterm labor." Obstetrics & Gynecology 101.2 (2003): 402-412. (Year: 2003).*
Communication dated May 8, 2018, from the European Patent Office in counterpart European Application No. 17190040.0.
E. Hernandez-Andrade et al. "Evaluation of cervical stiffness during pregnancy using semiquantitative ultrasound elastography" Ultrasound in Obstetrics and Gynecology, vol. 41, No. 2, Jan. 8, 2013 (pp. 152-161) XP055471210.
Brandi N. Briggs et al. "A Hertzian contact mechanics based formulation to improve ultrasound elastography assessment of uterine cervical tissue stiffness" Journal of Biomechanics, vol. 48, No. 9, Apr. 29, 2015 (pp. 1524-1532) XP029236617.
Edgar Hernandez-Andrade et al. "Cervical strain determined by ultrasound elastography and its association with spontaneous preterm delivery" Journal of Perinatal Medicine, vol. 42, No. 2, Jan. 1, 2014 (pp. 159-169) XP055471141.
F. S. Molina et al. "Quantification of cervical elastography: a reproducibility study" Ultrasound in Obstetrics and Gynecology, vol. 39, No. 6, May 22, 2012 (pp. 685-689) XP055471068.
Edgar Hernandez-Andrade et al. Strain at the internal cervical os assessed with quasi-static elastography is associated with the risk of spontaneous preterm delivery at ≤ 34 weeks of gestation Journal of Perinatal Medicine, vol. 43, No. 6, Nov. 1, 2015 (18 pages total) XP055471090.
Syun-ichi Yamaguchi et al. "Tissue elastography imaging of the uterine cervix during pregnancy" Journal of Medical Ultrasonics, vol. 34, No. 4, Dec. 14, 2007 (pp. 209-210) XP019547370.

\* cited by examiner

ULTRASOUND IMAGING APPARATUS AND ULTRASOUND IMAGE DISPLAY METHOD

CROSS-REFERENCE TO RELATED APPLICATION

This application claims the benefit of Korean Patent Application No. 10-2017-0008684, filed on Jan. 18, 2017, in the Korean Intellectual Property Office, the disclosure of which is incorporated herein in its entirety by reference.

BACKGROUND

1. Field

One or more embodiments relate to ultrasound imaging apparatuses, ultrasound image display methods, and computer-readable recording media storing program codes for executing the ultrasound image display methods.

2. Description of the Related Art

Ultrasound imaging apparatuses obtain at least one image of a portion in an object, for example, soft tissue or a blood flow, by irradiating ultrasound signals generated by a transducer of a probe onto the object and receiving information of signals reflected from the object.

SUMMARY

One or more embodiments include ultrasound imaging apparatuses and ultrasound image display methods, by which the risk of premature birth may be more accurately determined by more accurately setting a region of interest (ROI) of an internal orifice of the uterus (IOS) and a ROI of an external orifice of the uterus (EOS).

One or more embodiments include ultrasound imaging apparatuses and ultrasound image display methods, by which a user may more easily check the risk of premature birth by providing a degree of elasticity in the set ROI of the IOS and the set ROI of the EOS in various methods.

Additional aspects will be set forth in part in the description which follows and, in part, will be apparent from the description, or may be learned by practice of the presented embodiments.

According to one or more embodiments, an ultrasound imaging apparatus includes a processor configured to set an internal orifice of an uterus (IOS) point indicating the IOS of a cervix and an external orifice of an uterus (EOS) point indicating the EOS of the cervix, from a cervix line indicating a cervical canal, set a region of interest (ROI) of the IOS and a ROI of the EOS based on the IOS point and the EOS point, and calculate degrees of elasticity in the ROI of the IOS and the ROI of the EOS, and a display configured to display information indicating the degrees of elasticity in the ROI of the IOS and the ROI of the EOS.

The processor may set a ROI of the cervix including the ROI of the IOS and the ROI of the EOS, and calculate a degree of elasticity in the ROI of the cervix, and the display may display information indicating the degree of elasticity in the ROI of the cervix.

The processor may generate a first guide line and a second guide line, each having a start point at the IOS point, and set the ROI of the IOS based on the IOS point and endpoints of the first guide line and the second guide line, and generate a third guide line and a fourth guide line, each having a start point at the EOS point, and set the ROI of the EOS based on the EOS point and endpoints of the third guide line and the fourth guide line.

The processor may determine a ROI of the cervix based on the endpoints of the first guide line, the second guide line, the third guide line, and the fourth guide line, and the cervix line.

The processor may determine the ROI of the cervix by connecting the endpoints of the first guide line, the second guide line, the third guide line, and the fourth guide line, the IOS point, and the EOS point, and a line connecting the endpoint of the first guide line and the endpoint of the third guide line and a line connecting the endpoint of the second guide line and the endpoint of the fourth guide line each have a shape of the cervix line.

The processor may receive an external input to adjust positions of the endpoints of the first guide line and the second guide line, set the ROI of the IOS based on the endpoint of the first guide line and the endpoint of the second guide line, whose positions are adjusted, and the IOS point, receive an external input to adjust the positions of the endpoints of the third guide line and the fourth guide line, and set the ROI of the EOS based on the endpoint of the third guide line and the endpoint of the fourth guide line, whose positions are adjusted, and the EOS point.

The processor may set the ROI of the IOS and the ROI of the EOS to have a fan shape or a polygonal shape.

The display may display information about the ROI of the IOS and the ROI of the EOS in an elastography image with respect to an object to be overlapped on an ultrasonic image.

The processor may calculate a cervical length based on the cervix line, and the display may display the cervical length with the information indicating the degrees of elasticity in the ROI of the IOS and the ROI of the EOS.

The processor may determine a risk of premature birth based on the degrees of elasticity in the ROI of the IOS and the ROI of the EOS, and the cervical length, and the display may output a result of the determination of the risk of premature birth.

The ultrasound imaging apparatus may further include a data acquirer configured to acquire ultrasound data about an object including the cervix, wherein the processor generates an ultrasonic image based on the acquired ultrasound data.

According to one or more embodiments, an ultrasound image display method includes setting an internal orifice of an uterus (IOS) point indicating the IOS of a cervix and an external orifice of an uterus (EOS) point indicating the EOS of the cervix, from a cervix line indicating a cervical canal, setting a region of interest (ROI) of the IOS and a ROI of the EOS based on the IOS point and the EOS point, calculating degrees of elasticity in the ROI of the IOS and the ROI of the EOS, and displaying information indicating the degrees of elasticity in the ROI of the IOS and the ROI of the EOS.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
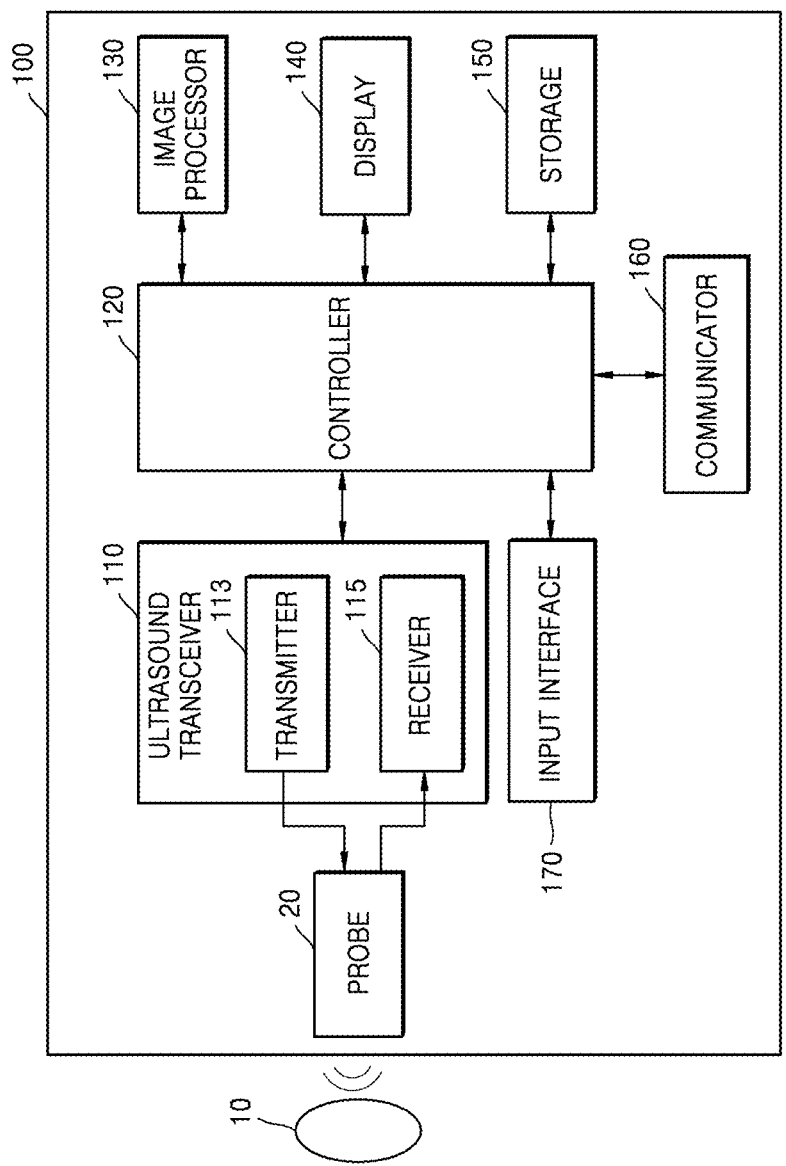
FIG. 1 is a block diagram of a configuration of an ultrasound imaging apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, the term "image" may refer to multi-dimensional data composed of discrete image elements. For example, an image may be a medical image (an ultrasound image, a computed tomography (CT) image, or a magnetic resonance imaging (MRI) image) of an object acquired by an ultrasound imaging apparatus, a CT apparatus, an MRI apparatus, or another medical imaging apparatus.

An "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom, which is a material having a density, an effective atomic number, and a volume that are approximately the same as those of an organism. For example, the phantom may be a spherical phantom having properties similar to a human body.

An ultrasound image may be an image obtained by transmitting ultrasound signals generated by transducers of a probe to an object and receiving echo signals reflected from the object. In addition, an ultrasound image may be variously implemented. For example, an ultrasound image may be at least one of an amplitude mode (A mode) image, a brightness mode (B mode) image, a color mode (C mode) image, and a Doppler mode (D mode) image. Furthermore, according to one or more embodiments, an ultrasound image may be a two-dimensional image or a three-dimensional image.

Throughout the specification, a "user" may be, but is not limited to, a medical expert, for example, a medical doctor, a nurse, a medical laboratory technologist, or a medical imaging expert, or a technician who repairs medical apparatuses.

Reference will now be made in detail to embodiments, examples of which are illustrated in the accompanying drawings. In this regard, the present embodiments may have different forms and should not be construed as being limited to the descriptions set forth herein.

FIG. 1 is a block diagram showing a configuration of an ultrasound imaging apparatus 100 according to an embodiment.

Referring to FIG. 1, the ultrasound imaging apparatus 100 according to an embodiment may include a probe 20, an ultrasound transceiver 110, a controller 120, an image processor 130, a display 140, a storage 150, a communicator 160, and an input interface 170.

The ultrasound imaging apparatus 100 may be of a cart-type or a portable-type ultrasound imaging apparatus. Examples of the portable-type ultrasound imaging apparatus 100 may include a smartphone, a laptop computer, a personal digital assistant (PDA), and a tablet personal computer (PC), each of which may include a probe and an application, but embodiments are not limited thereto.

The probe 20 may include a plurality of transducers. The plurality of transducers may transmit ultrasound signals to an object 10 in response to transmitting signals applied by a transmitter 113. The plurality of transducers may receive ultrasound signals reflected from the object 10 to generate reception signals. In addition, the probe 20 and the ultrasound imaging apparatus 100 may be formed in one body, or the probe 20 and the ultrasound imaging apparatus 100 may be formed separately but linked wirelessly or via wires. In addition, the ultrasound imaging apparatus 100 may include one or more probes 20 according to embodiments.

The controller 120 may control the transmitter 113 to generate transmitting signals to be applied to each of the plurality of transducers based on a position and a focal point of the plurality of transducers included in the probe 20.

The controller 120 may control the receiver 115 to generate ultrasound data by converting reception signals received from the probe 20 from analogue to digital signals and summing the digital reception signals based on a position and a focal point of the plurality of transducers.

The image processor 130 may generate an ultrasound image by using ultrasound data generated from the receiver 115. For example, the image processor 130 may generate an ultrasound image by using envelope information extracted from the receiver 115.

The display 140 may display the generated ultrasound image and various pieces of information processed by the ultrasound imaging apparatus 100. The ultrasound imaging apparatus 100 may include two or more displays 140 according to embodiments. The display 140 may include a touch screen in combination with a touch panel.

The controller 120 may control the operations of the ultrasound imaging apparatus 100 and flow of signals between the internal elements of the ultrasound imaging apparatus 100. The controller 120 may include a memory for storing a program or data to perform functions of the ultrasound imaging apparatus 100 and a processor and/or a microprocessor (not shown) for processing the program or data. For example, the controller 120 may control the operation of the ultrasound imaging apparatus 100 by receiving a control signal from the input interface 170 or an external apparatus.

The ultrasound imaging apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatus. For example, the communicator 160 may include at least one among a short-range communication module, a wired communication module, and a wireless communication module.

The communicator 160 may receive a control signal and data from an external apparatus and transmit the received control signal to the controller 120, so that the controller 120 may control the ultrasound imaging apparatus 100 in response to the received control signal.

The controller 120 may transmit a control signal to an external apparatus via the communicator 160 so that the external apparatus may be controlled in response to the control signal of the controller 120.

For example, the external apparatus connected to the ultrasound imaging apparatus 100 may process data of the external apparatus in response to control signal of the controller 120 received via the communicator 160.

A program for controlling the ultrasound imaging apparatus 100 may be installed in the external apparatus. The program may include command languages to perform part of operation of the controller 120 or the entire operation of the controller 120.

The program may be pre-installed in the external apparatus or may be installed by a user of the external apparatus by downloading the program from a server that provides applications. The server that provides applications may include a recording medium where the program is stored.

The storage 150 may store various pieces of data or programs for driving and controlling the ultrasound imaging apparatus 100, input and/or output ultrasound data, ultrasound images, applications, etc.

The input interface 170 may receive a user's input to control the ultrasound imaging apparatus 100 and may include a keyboard, button, keypad, mouse, trackball, jog switch, knob, a touchpad, a touch screen, a microphone, a motion input means, a biometrics input means, etc. For example, the user's input may include inputs for manipulating buttons, keypads, mice, track balls, jog switches, or knobs, inputs for touching a touchpad or a touch screen, a voice input, a motion input, and a bioinformation input, for example, iris recognition or fingerprint recognition, but an exemplary embodiment is not limited thereto.

An example of the ultrasound imaging apparatus 100 according to the present exemplary embodiment is described below with reference to FIGS. 2A, 2B, and 2C.

Figure 2C:
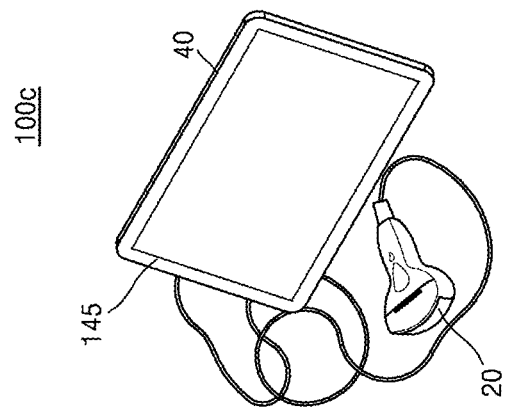
FIGS. 2A, 2B, and 2C are diagrams illustrating ultrasound imaging apparatuses according to various embodiments.
Figure 2B:
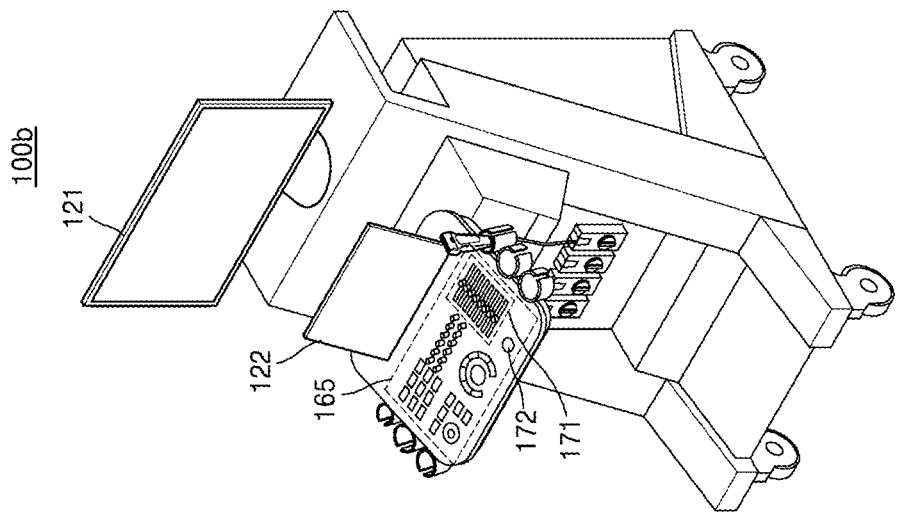
Figure 2A:
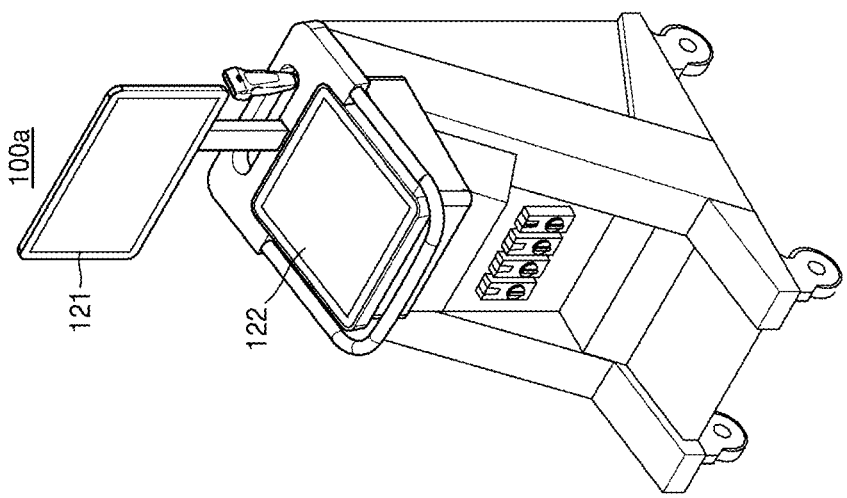

FIGS. 2A, 2B, and 2C are diagrams illustrating ultrasound imaging apparatuses 100a, 100b, and 100c according to various embodiments.

Referring to FIGS. 2A and 2B, each of ultrasound imaging apparatuses 100a and 100b may include a main display 121 and a sub-display 122. At least one among the main display 121 and the sub-display 122 may include a touch screen. The main display 121 and the sub-display 122 may display ultrasound images and/or various information processed by the ultrasound imaging apparatuses 100a and 100b. The main display 121 and the sub-display 122 may provide graphical user interfaces (GUI), thereby receiving user's inputs of data to control the ultrasound imaging apparatuses 100a and 100b. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound imaging apparatuses 100a and 100b may control the display of the ultrasound image on the main display 121 by using the input control data.

Referring to FIG. 2B, the ultrasound imaging apparatus 100b may include a control panel 165. The control panel 165 may include buttons, trackballs, jog switches, or knobs, and may receive data to control the ultrasound imaging apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected during scanning an ultrasound image, the ultrasound imaging apparatus 100b may keep displaying a frame image at that time point.

The buttons, trackballs, jog switches, and knobs included in the control panel 165 may be provided as a GUI to the main display 121 or the sub-display 122.

Referring to FIG. 2C, the ultrasound imaging apparatus 100c may include a portable device. An example of the portable ultrasound imaging apparatus 100c may include, for example, smart phones including probes and applications, laptop computers, personal digital assistants (PDAs), or tablet PCs, but the present disclosure is not limited thereto.

The ultrasound imaging apparatus 100c may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound imaging apparatus 100, and a GUI.

Figure 3:
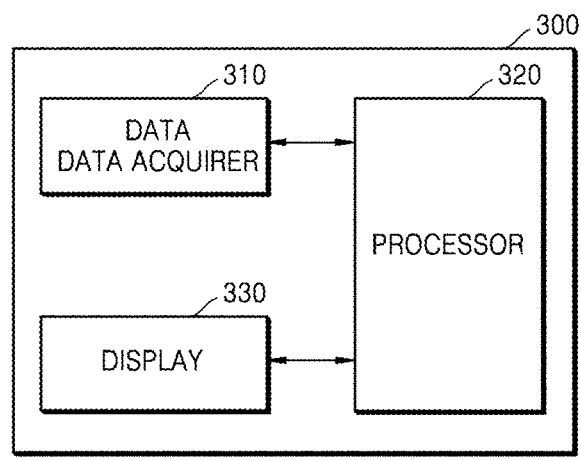
FIG. 3 is a block diagram of a configuration of an ultrasound imaging apparatus according to an embodiment.

FIG. 3 is a block diagram of a configuration of an ultrasound imaging apparatus 300 according to an embodiment.

The ultrasound imaging apparatus 300 according to the present embodiment may include a processor 320 and a display 330. In some embodiments, the ultrasound imaging apparatus 300 may further include a data acquirer 310, in addition to the processor 320 and the display 330.

The processor 320 of FIG. 3 may correspond to at least one of the image processor 130 and the controller 120 FIG. 1, or to a combination thereof. The display 330 may correspond to the display 140 of FIG. 1. The data acquirer 310 may include the probe 20 of FIG. 1. Furthermore, according to an embodiment, some of the elements of the ultrasound imaging apparatus 100 of FIG. 1 may be included in the ultrasound imaging apparatus 300 of FIG. 3.

According to an embodiment, the data acquirer 310 may acquire ultrasound data about an object including the cervix. For example, the data acquirer 310 may irradiate ultrasound waves toward the object and detect an echo signal, by using the probe 20.

The processor 320 may control an overall operation of the ultrasound imaging apparatus 300 and process data and signals. The processor 320 may include at least one hardware unit. The processor 320 according to an embodiment may include a separated hardware unit that functions as an image processor and a controller. The processor 320 may be operated by one or more software module generated by executing program codes stored in memory.

The processor 320 according to an embodiment sets an internal orifice of the uterus (IOS) point indicating the IOS of the cervix and an external orifice of the uterus (EOS) point indicating the EOS of the cervix, from a cervix line indicating a cervical canal.

For example, the processor 320 may receive an external input to select a plurality of points according to the shape of the cervical canal in an ultrasonic image showing the object including the cervix. The processor 320 may determine a cervix line based on the selected points. The processor 320 may set an IOS point and an EOS point from the determined cervix line. For example, the processor 320 may set points located at opposite ends of the points selected according to the shape of the cervical canal to be the IOS point and the EOS point.

The processor 320 according to an embodiment may set regions of interest of the IOS and the EOS based on the IOS point and the EOS point.

The processor 320 may generate guide lines based on the IOS point to set a region of interest (ROI) of the IOS. For example, the processor 320 may automatically generate a first guide line and a second guide line, each having a start point at the IOS point. For example, the first guide line may be generated to have a start point at the IOS point in a direction perpendicular to the cervix line, and the second guide line may be generated to have a start point at the IOS point in a direction opposite to the direction of the first guide line.

The processor 320 may set a ROI of the IOS that the user desires, by adjusting the positions of endpoints of the first guide line and the second guide line. For example, the processor 320 may receive an external input to adjust the position of the endpoint of the first guide line. For example, the processor 320 may receive an external input to move the endpoint of the first guide line to a position indicating a boundary of the cervix, and in response to the received external input, may move the position of the endpoint of the first guide line. Furthermore, the processor 320 may receive an external input to move the endpoint of the second guide line, and in response to the received external input, may move the position of the endpoint of the second guide line. For example, the processor 320 may move the endpoint of the second guide line to a position indicating another boundary of the cervix. Accordingly, the processor 320 may move the endpoint of the first guide line and the endpoint of the second guide line to the positions indicating the boundaries of the cervix.

The processor 320 according to an embodiment may set a ROI of the IOS based on the IOS point, the endpoint of the first guide line, and the endpoint of the second guide line. For example, the ROI of the IOS may be set to have a fan shape having the center of a circle at the IOS point. However, according to embodiments, the ROI of the IOS may be set to have a polygonal shape, but the present disclosure is not limited thereto.

A ROI of the EOS may be set in a method similar to the method of setting the ROI of the IOS.

The processor 320 may generate guide lines based on the EOS point in order to set the ROI of the EOS. For example, the processor 320 may automatically generate a third guide line and a fourth guide line, each having a start point at the EOS point. For example, the third guide line may be generated to have a start point at the EOS point in a direction perpendicular to the cervix line, and the fourth guide line may be generated to have a start point at the IOS point in a direction opposite to the direction of the third guide line.

The processor 320 may set a ROI of the EOS that the user desires, by adjusting the position of endpoints of the third guide line and the fourth guide line. For example, the processor 320 may move the endpoints of the third guide line and the fourth guide line to the positions indicating the boundaries of the cervix, based on the external input. A detailed description thereof is presented below with reference to FIGS. 7A and 7B.

The processor 320 according to an embodiment may set a ROI of the EOS based on the EOS point, the endpoint of the third guide line, and the endpoint of the fourth guide line. For example, the ROI of the EOS may be set to have a fan shape having the center of a circle at the EOS point.

The processor 320 according to an embodiment may determine a ROI of the cervix including the ROI of the IOS and the ROI of the EOS.

The processor 320 according to an embodiment may set the ROI of the cervix based on the cervix line, the endpoints of the first and second guide lines used to set the ROI of the IOS, and the endpoints of the third and fourth guide lines used to set the ROI of the EOS. For example, the processor 320 may determine the ROI of the cervix by connecting the IOS point, the EOS point, and the endpoints of the first guide line, the second guide line, the third guide line, and the fourth guide line. In this state, the processor 320 may connect the endpoints of first guide line and the third guide line such that a line connecting the endpoints of the first and third guide lines may have a form of the cervix line. Furthermore, the processor 320 may connect the endpoints of second guide line and the fourth guide line such that a line connecting the endpoints of the second and fourth guide lines may have a form of the cervix line.

The processor 320 according to an embodiment may calculate degrees of elasticity in the ROI of the IOS and the ROI of the EOS. For example, the processor 320 may extract information about the ROI of the IOS and the ROI of the EOS from an elastography image showing the same object as the ultrasonic image. Alternatively, the processor 320 may calculate a representative value representing a degree of elasticity of each region with respect to the ROI of the IOS and the ROI of the EOS. For example, each representative value may signify an average of elasticity values of each region.

The processor 320 according to an embodiment may calculate the cervical length based on the cervix line. Furthermore, the processor 320 may determine the risk of premature birth based on the degrees of elasticity in the ROI of the IOS and the ROI of the EOS and the cervical length.

The display 330 may display an operation state of the ultrasound imaging apparatus 300, the ultrasonic image, and a user interface screen. The display 330 may include one or more display panels according to embodiments. According to an embodiment, the display 330 may be implemented in form of a touch screen.

The display 330 according to an embodiment may display information indicating the degrees of elasticity in the ROI of the IOS and the ROI of the EOS. Furthermore, the display 330 may display information indicating a degree of elasticity in the ROI of the cervix. For example, the display 330 may display the elasticity value in each ROI in form of text, or in a preset color corresponding to the elasticity value. According to another embodiment, the display 330 may display the information about the ROI of the IOS and the ROI of the EOS in the elastography image to be overlapped with the ultrasonic image. Alternatively, the display 330 may display the ROI of the IOS and the ROI of the EOS in a preset color according to the representative value representing the degree of elasticity in each of the ROI of the IOS and the ROI of the EOS.

The display 330 according to an embodiment may display the cervical length with information indicating the degrees of elasticity in the ROI of the IOS and the ROI of the EOS. Accordingly, the ultrasound imaging apparatus 300 may enable the user to check information needed for determining the risk of premature birth. Furthermore, the display 330 may output a result of the risk of premature birth determined by the processor 320.

Figure 4:
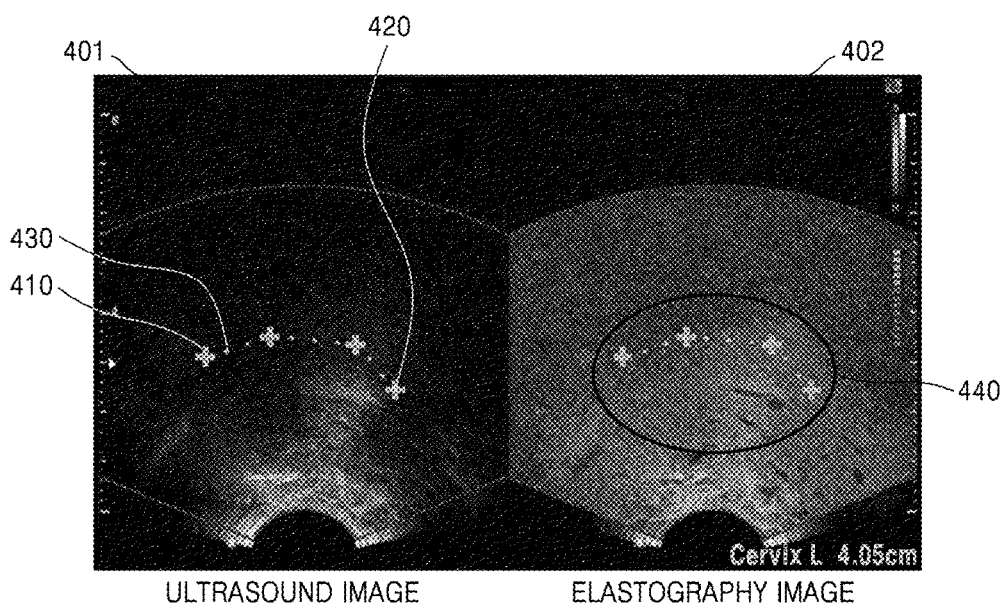
FIG. 4 is an image showing a process of marking a cervix line, according to an embodiment.

FIG. 4 is an image showing a process of marking the cervix line, according to an embodiment.

The ultrasound imaging apparatus 300 according to an embodiment may receive an external input to select a plurality of points according to the shape of the cervical canal in the ultrasonic image showing the object including the cervix. For example, as illustrated in FIG. 4, the ultrasound imaging apparatus 300 may receive external inputs to select four (4) points in an ultrasonic image 401 according to the shape of the cervical canal.

The ultrasound imaging apparatus 300 may display a cervix line 430 based on the four points selected through the external input. For example, the ultrasound imaging apparatus 300 may display the cervix line 430 by connecting the selected four points.

The ultrasound imaging apparatus 300 according to an embodiment may set two points at the opposite ends of the cervix line 430, respectively, to be an IOS point 410 and an EOS point 420. The IOS point 410 may signify a point indicating the internal OS of the cervix, whereas the EOS point 420 may signify a point indicating the external OS of the cervix. For example, among the points illustrated in FIG. 4, the processor 320 may set a point located inside the cervix to be the IOS point 410 and a point located outside the cervix to be the EOS point 420.

When displaying both the ultrasonic image 401 and the elastography image 402, the ultrasound imaging apparatus 300 according to an embodiment may display the points selected in the ultrasonic image 401, also in the elastography image 402. Furthermore, when the cervix line 430 is displayed on the ultrasonic image 401, the ultrasound imaging apparatus 300 may display the cervix line at a position corresponding to the elastography image 402 (440).

Figure 5A:
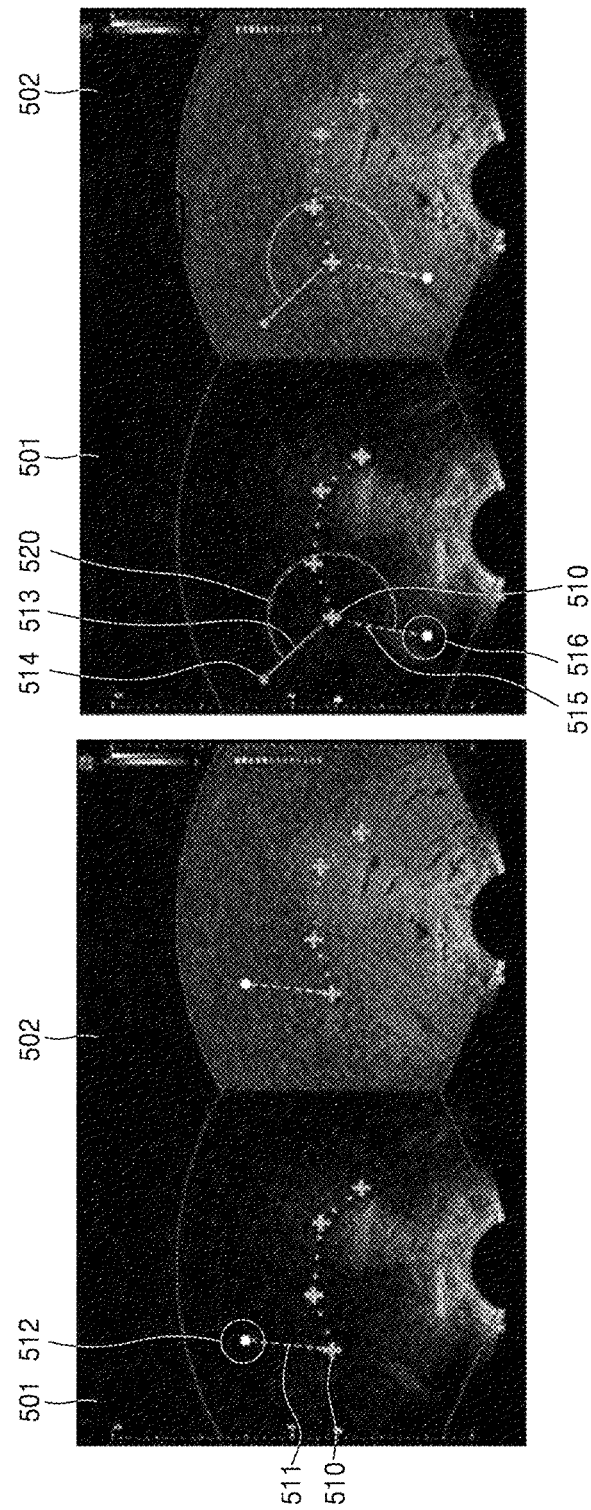
FIGS. 5A and 5B are images showing a process of setting a region of interest (ROI) of an internal orifice of the uterus (IOS), according to an embodiment.
Figure 5B:
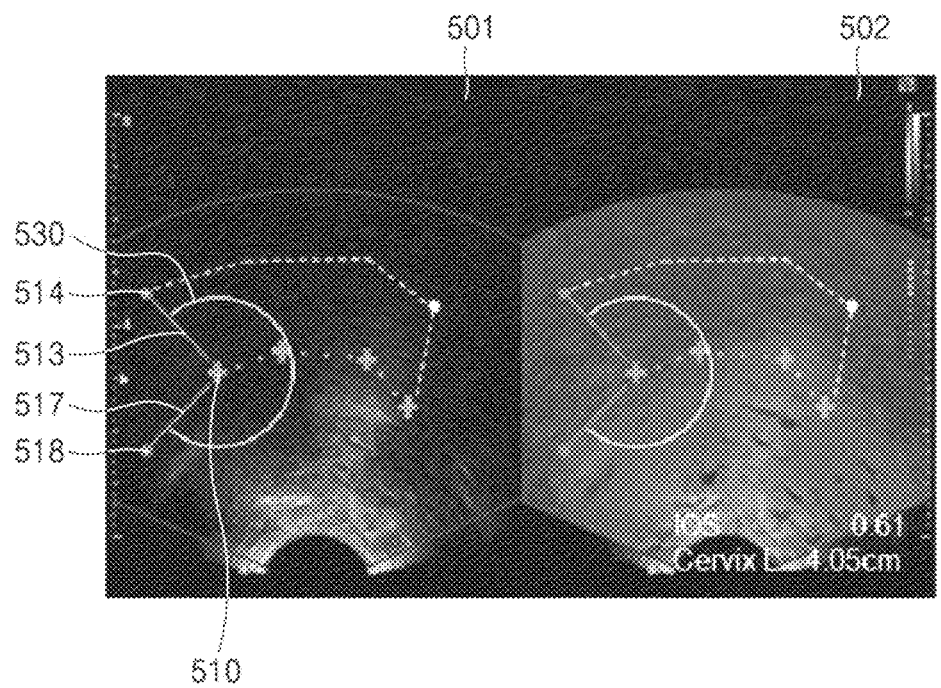

FIGS. 5A and 5B are images showing a process of setting the ROI of the IOS, according to an embodiment.

The ultrasound imaging apparatus 300 according to an embodiment may compare degrees of elasticity between the IOS and the EOS to determine the risk of premature birth. In order to compare the degrees of elasticity between the IOS and the EOS, a process of setting the ROI of the IOS and the ROI of the EOS is necessary.

The ultrasound imaging apparatus 300 according to an embodiment may generate guide lines to set the ROI of the IOS. For example, referring to FIG. 5A, a first guide line 511 needed to set the ROI of the IOS may be automatically generated with a start point at an IOS point 510 indicating the IOS in an ultrasonic image 501. For example, as illustrated in FIG. 5A, the first guide line 511 may be generated in a direction perpendicular to the cervix line from the IOS point 510 as a start point. According to an embodiment, the first guide line 511 may be generated in a direction preset by the ultrasound imaging apparatus 300 from the IOS point 510 as a start point.

The ultrasound imaging apparatus 300 according to an embodiment the position of an endpoint 512 of the first guide line 511 to set the ROI of the IOS in a shape desired by the user. In this state, the ultrasound imaging apparatus 300 may move the endpoint 512 of the first guide line 511 to an adjusted position in response to an external input to adjust the position of the endpoint 512 of the first guide line 511. For example, the ultrasound imaging apparatus 300 may receive an external input to move the endpoint 512 of the first guide line 511 to a position indicating the boundary of the cervix. The external input may be an input to move the position of the endpoint 512 of the first guide line 511 by using, for example, a trackball. Alternatively, when the display 330 displaying the ultrasonic image 501 is implemented by a touch screen, the external input may include a pressure of touching a certain position.

Furthermore, referring to FIG. 5A, the ultrasound imaging apparatus 300 may automatically generate a second guide line 515 needed to set the ROI of the IOS having a center at the IOS point 510 indicating the IOS in the ultrasonic image 501. For example, the second guide line 515 may be generated in a direction opposite to the direction of the first guide line 511, from the IOS point 510 as a center point.

As the second guide line 515 is automatically generated, the ultrasound imaging apparatus 300 may display an expected ROI of the IOS 520 based on an endpoint 514 of a first guide line 513 and an endpoint 516 of the second guide line 515, whose positions are adjusted. Since the ROI of the IOS is not fixed, the ultrasound imaging apparatus 300 may display the expected ROI of the IOS 520 to be distinguished from a fixed ROI of the IOS. For example, referring to FIG. 5A, the ultrasound imaging apparatus 300 may indicate the expected ROI of the IOS 520 by using a dotted line in order to show that the expected ROI of the IOS 520 is not the fixed ROI of the IOS.

When displaying both of the ultrasonic image 501 and an elastography image 502, the ultrasound imaging apparatus 300 according to an embodiment may display, on the elastography image 502, the IOS point 510, the first guide lines 511 and 513, the second guide line 515, and the expected ROI of the IOS 520, which are displayed on the ultrasonic image 501.

The ultrasound imaging apparatus 300 according to an embodiment may receive an external input to adjust the position of the endpoint 516 of the second guide line 515, to set the ROI of the IOS as the user desires. For example, the ultrasound imaging apparatus 300 may receive an external input to move the endpoint 516 of the second guide line 515 to a position indicating the boundary of the cervix. The ultrasound imaging apparatus 300, in response to the received external input, may move the position of the endpoint 516 of the second guide line 515.

Referring to FIG. 5B, the ultrasound imaging apparatus 300 may set a ROI of the IOS 530 based on the endpoint 514 of the first guide line 513 and an endpoint 518 of a second guide line 517, whose positions are adjusted, and the IOS point 510. For example, the ROI of the IOS 530 may have a fan shape having the center of a circle at the IOS point 510. In this state, the radius of the circle may be a value preset according to an internal instruction of the ultrasound imaging apparatus 300. For example, the ROI of the IOS 530 may be set to have a fan shape having the center of a circle at the IOS point 510 and the radius of about 1 cm, but the present disclosure is not limited thereto. In some embodiments, the radius of the circle may be changed according to the external input, and the ROI of the IOS 530 may be set to have a polygonal shape not a circular shape.

The ultrasound imaging apparatus 300 according to an embodiment may display the ROI of the IOS 530 that is set. For example, the ultrasound imaging apparatus 300 may set the ROI of the IOS 530, which is set based on the endpoint 514 of the first guide line 513 and the endpoint 518 of the second guide line 517, whose positions are adjusted, to be a fixed ROI of the IOS. Furthermore, the ultrasound imaging apparatus 300 may display the fixed ROI of the IOS to be distinguished from an expected ROI of the IOS. For example, the ultrasound imaging apparatus 300 may display the fixed ROI of the IOS by using a solid line or by using a certain color for highlight.

Figure 6A:
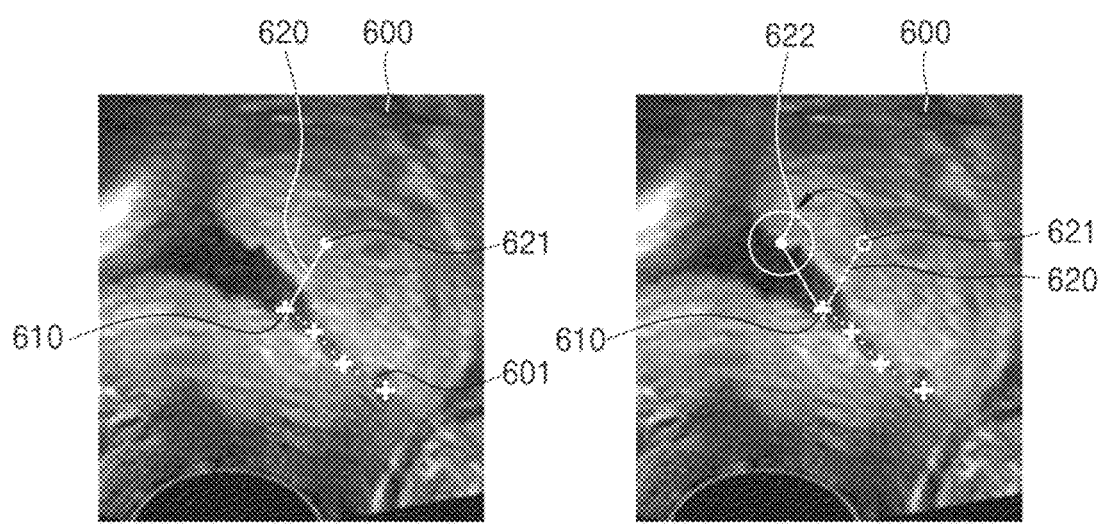
FIGS. 6A and 6B are images showing a process of setting a ROI of an IOS, according to another embodiment.
Figure 6B:
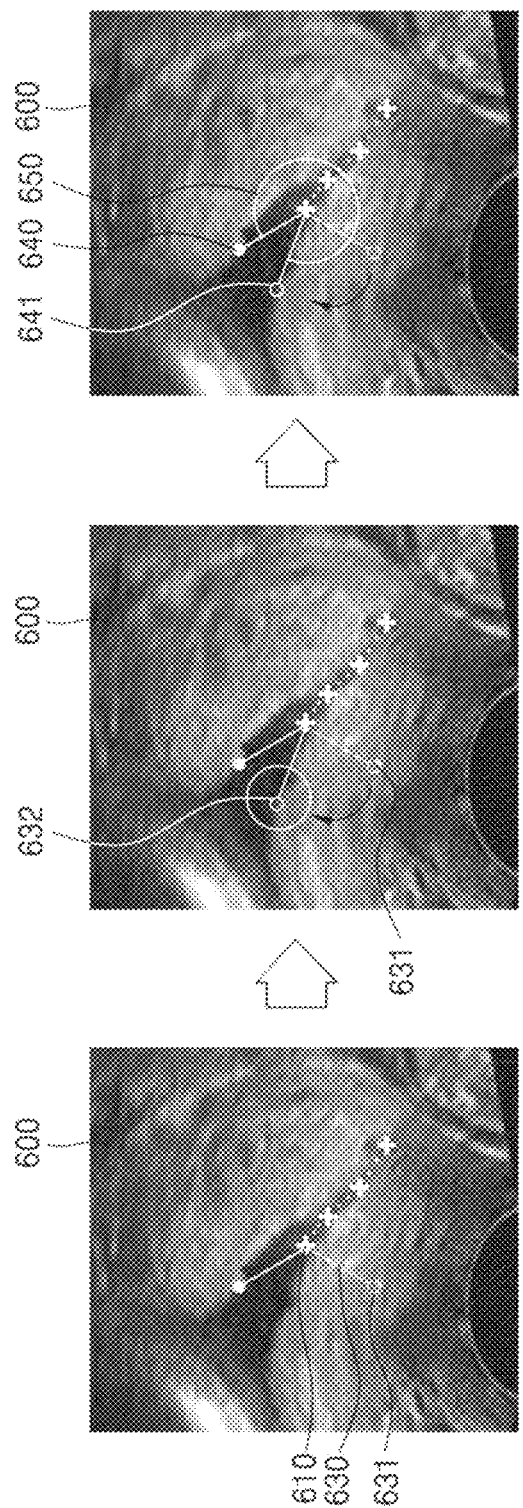

FIGS. 6A and 6B are images showing a process of setting a ROI of the IOS, according to another embodiment.

The ultrasound imaging apparatus 300 according to an embodiment may set a ROI of the IOS based on the endpoints of the first and second guide lines, and the IOS point. Accordingly, the ROI of the IOS may be set differently according to the positions of the endpoints of the first and second guide lines. In order to more accurately set the ROI of the IOS, the ultrasound imaging apparatus 300 may adjust the positions of the endpoint of the first guide line and the endpoint of the second guide line needed to set the ROI of the IOS. For example, in order to set an area corresponding to the IOS of the cervix to be a ROI of the IOS in the ultrasonic image, the ultrasound imaging apparatus 300 may adjust the endpoint of the first guide line and the endpoint of the second guide line to be located at positions indicating the boundary of the cervix.

For example, referring to FIG. 6A, the ultrasound imaging apparatus 300 may automatically generate a first guide line 620 having a start point at an IOS point 610 in an ultrasonic image 600. For example, the first guide line 620 may be generated in a direction perpendicular to a cervix line 601 from the IOS point 610 as a start point. In this state, the ultrasound imaging apparatus 300 may move an endpoint 621 of the first guide line 620 to a position 622 indicating the boundary of the cervix.

Furthermore, referring to FIG. 6B, the ultrasound imaging apparatus 300 may automatically generate a second guide line 630 having a start point at the IOS point 610 in the ultrasonic image 600. The ultrasound imaging apparatus 300 may move an endpoint 631 of the second guide line 630 that is automatically generated to a position 632 indicating the boundary of the cervix.

The ultrasound imaging apparatus 300 according to an embodiment may set a ROI of the IOS 650 based on an endpoint 640 of the first guide line and an endpoint 641 of the second guide line, whose positions are adjusted, and the IOS point 610. Accordingly, the ultrasound imaging apparatus 300 may more accurately set a ROI of the IOS needed for determining the risk of premature birth, by adjusting the positions of the endpoint 621 of the first guide line 620 and the endpoint 631 of the second guide line 630, which are automatically generated.

Figure 7A:
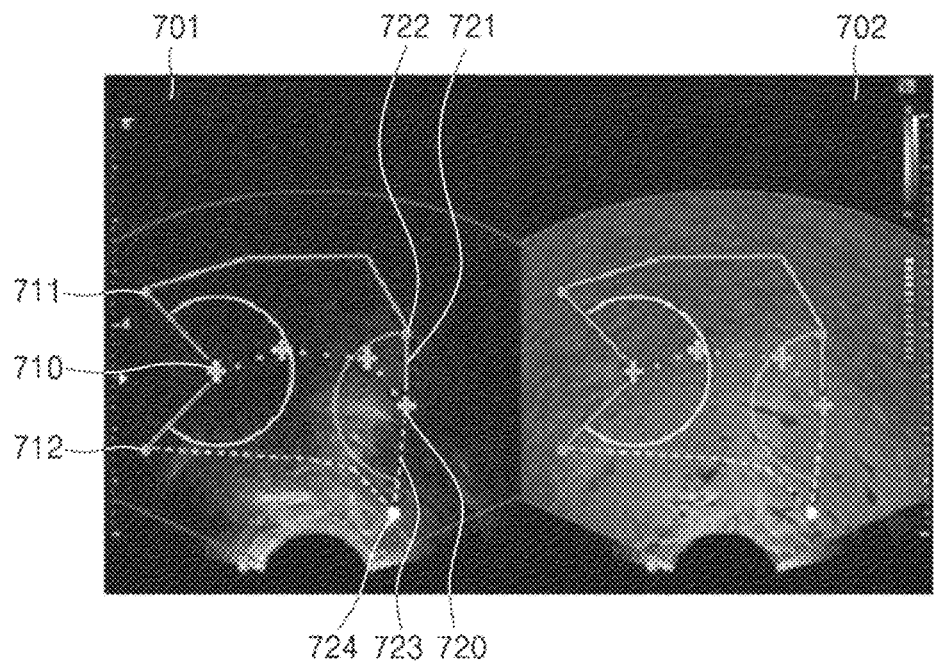
FIGS. 7A and 7B are images showing a process of setting a ROI of an external orifice of the uterus (EOS), according to an embodiment.
Figure 7B:
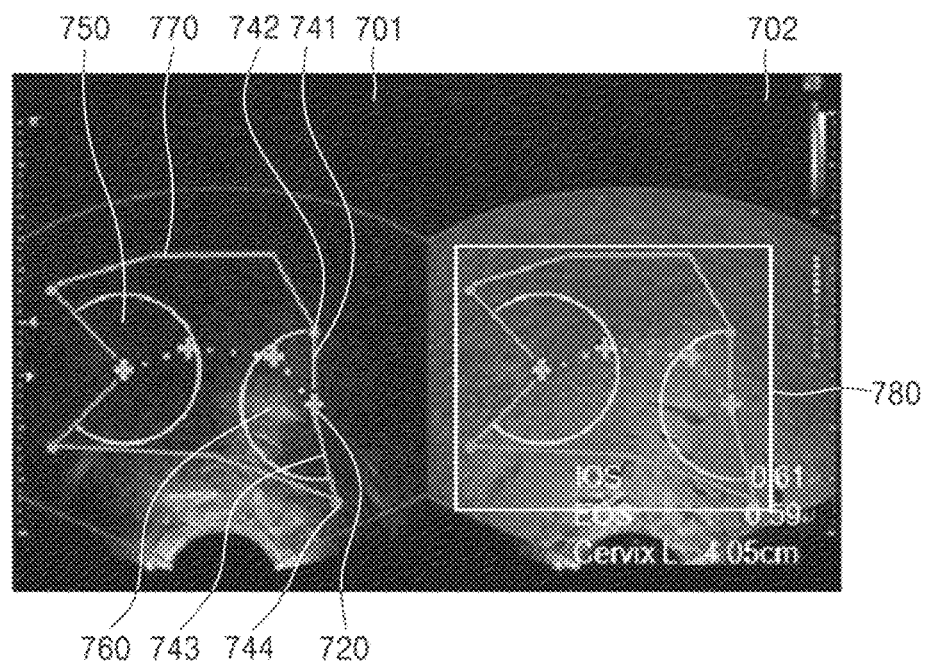

FIGS. 7A and 7B are images showing a process of setting a ROI of the EOS, according to an embodiment.

The ultrasound imaging apparatus 300 according to an embodiment may generate guide lines to set the ROI of the EOS. For example, the ultrasound imaging apparatus 300 automatically generate a third guide line needed to set the ROI of the EOS having a center at the EOS point indicating the EOS in the ultrasonic image. The ultrasound imaging apparatus 300 may receive an external input to move the position of an end portion of the third guide line, in order to set the ROI of the EOS in a form as the user desires.

Referring to FIG. 7A, the ultrasound imaging apparatus 300 according to an embodiment may automatically generate a third guide line 721 having a start point at an EOS point 720 in an ultrasonic image 701. The ultrasound imaging apparatus 300 may move the endpoint 722 of the third guide line 721 in response to an external input to adjust the position of an endpoint 722 of the third guide line 721. Furthermore, the ultrasound imaging apparatus 300 may automatically generate a fourth guide line 723 with respect to the EOS point 720 as the position of the endpoint 722 of the third guide line 721 is adjusted.

Referring to FIG. 7B, the ultrasound imaging apparatus 300 according to an embodiment may receive an external input to move the position of an endpoint 724 of the fourth guide line 723, to set the ROI of the EOS in a form as the user desires. The ultrasound imaging apparatus 300 may set a ROI of the EOS 760 based on an endpoint 742 of a third guide line 741 and an endpoint 744 of a fourth guide line 743, whose positions are adjusted, and the EOS point 720.

Furthermore, the ultrasound imaging apparatus 300 according to an embodiment may determine a ROI of the cervix 770 based on an IOS point 710 and the EOS point 720, the endpoint of a first guide line 711 having an adjusted position, the endpoint of the second guide line 712, the endpoint 742 of the third guide line 741, the endpoint 744 of the fourth guide line 743, and the ROI of the cervix 770. For example, the ultrasound imaging apparatus 300 may determine the ROI of the cervix 770 by connecting the IOS point 710 and the EOS point 720, the endpoints of the first guide line 711, the second guide line 712, the third guide line 741, and the fourth guide line 743. In this state, the ultrasound imaging apparatus 300 may connect the endpoint of the first guide line 711 and the endpoint 742 of the third guide line 741 such that a line connecting the endpoint of the first guide line 711 and the endpoint 742 of the third guide line 741 has a form of the cervix line. Furthermore, the ultrasound imaging apparatus 300 may connect the endpoint of the second guide line 712 and the endpoint 744 of the fourth guide line 743 such that a line connecting the endpoint of the second guide line 712 and the endpoint 744 of the fourth guide line 743 has a form of the cervix line.

The ultrasound imaging apparatus 300 according to an embodiment may display the determined ROI of the cervix 770 in the ultrasonic image 701 or the elastography image 702. Furthermore, when displaying both of the ultrasonic image 701 and the elastography image 702, the ultrasound imaging apparatus 300 may display a ROI of the IOS 750, the ROI of the EOS 760, and the ROI of the cervix 770 displayed in the ultrasonic image 701, also in the elastography image 702 (780).

Figure 8:
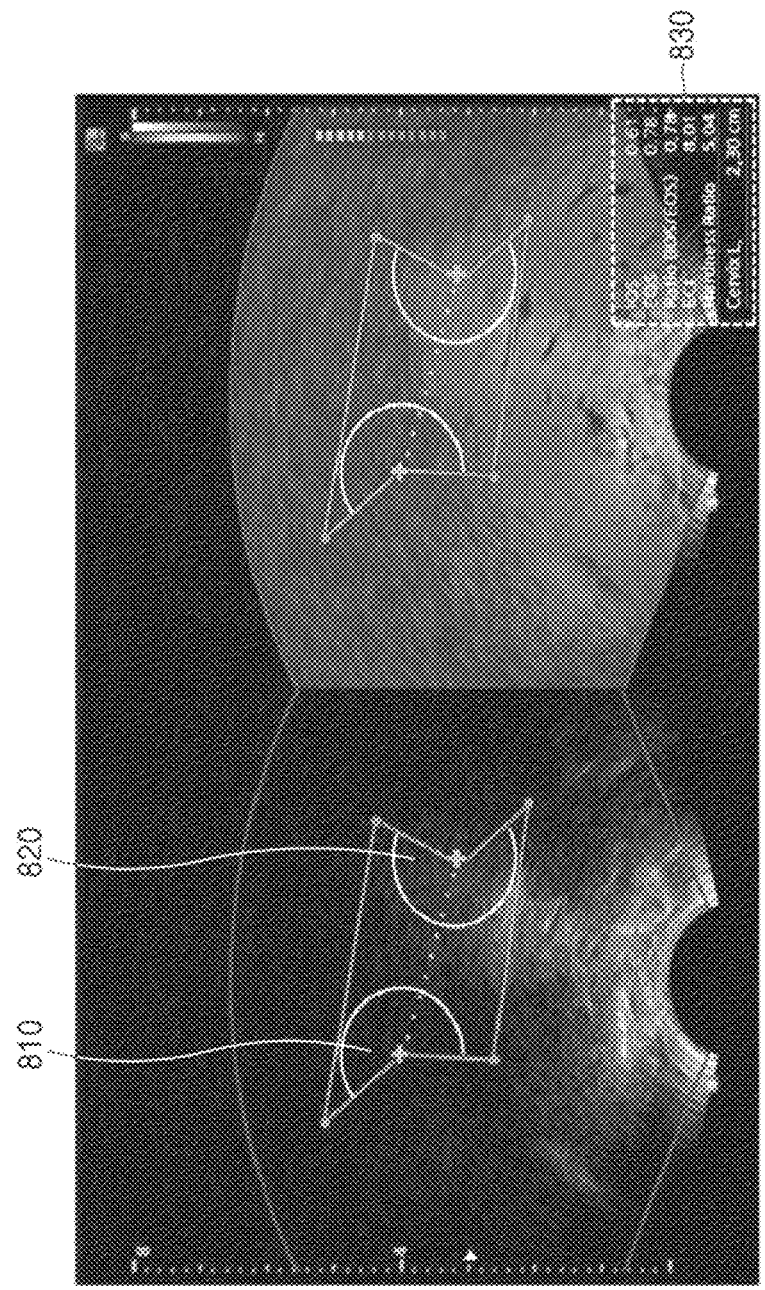
FIG. 8 is an image showing a process of displaying information indicating a degree of elasticity, according to an embodiment.

FIG. 8 is an image showing a process of displaying information indicating a degree of elasticity, according to an embodiment.

The ultrasound imaging apparatus 300 according to an embodiment may display information indicating a degree of elasticity in a ROI of the IOS 810 and a ROI of the EOS 820. For example, referring to FIG. 8, the ultrasound imaging apparatus 300 may display information indicating degrees of elasticity in the ROI of the IOS 810 and the ROI of the EOS 820 in a text format 830. For example, the information indicating the degree of elasticity may include a representative value representing the degrees of elasticity in the ROI of the IOS 810 and the ROI of the EOS 820 or a ratio of a degree of elasticity in the ROI of the IOS 810 to a degree of elasticity in the ROI of the EOS 820, but the present disclosure is not limited thereto. For example, the representative value may signify an average of the elasticity values.

The ultrasound imaging apparatus 300 according to an embodiment may calculate the cervical length from the cervix line, and display the calculated cervical length with the information indicating the degrees of elasticity in the ROI of the IOS 810 and the ROI of the EOS 820. For example, referring to FIG. 8, the ultrasonic imaging apparatus 300 may display in a text format 830 that the cervical length is 2.3 cm, the representative value indicating the degree of elasticity in the ROI of the IOS 810 is 0.61, the representative value representing the degree of elasticity in the ROI of the EOS 820 is 0.78, and a ratio of the degree of elasticity in the ROI of the IOS 810 to the degree of elasticity in the ROI of the EOS 820 is 0.78. Accordingly, as the ultrasound imaging apparatus 300 displays various pieces of information needed to determine the risk of premature birth, user convenience may be improved.

Furthermore, the ultrasound imaging apparatus 300 according to an embodiment may determine the risk of premature birth based on the degrees of elasticity in the ROI of the IOS 810 and the ROI of the EOS 820 and the cervical length. For example, the ultrasound imaging apparatus 300 may determine that the risk of premature birth is high as the degree of elasticity in the ROI of the EOS 820 is higher than the degree of elasticity in the ROI of the IOS 810. Furthermore, the ultrasound imaging apparatus 300 may determine that the risk of premature birth is high as the cervical length is less than a critical value. For example, assuming that a pregnant woman is at 18 to 22 weeks, if the cervical length is less than 25 mm, the ultrasound imaging apparatus 300 may determine that the risk of premature birth is over 50%, but the present disclosure is not limited thereto.

Furthermore, the ultrasound imaging apparatus 300 according to an embodiment may display a result of the determination of the risk of premature birth. For example, the ultrasound imaging apparatus 300 may display a result of the determination of the risk of premature birth by a percentage or a certain value, but the present disclosure is not limited thereto.

Figure 9A:
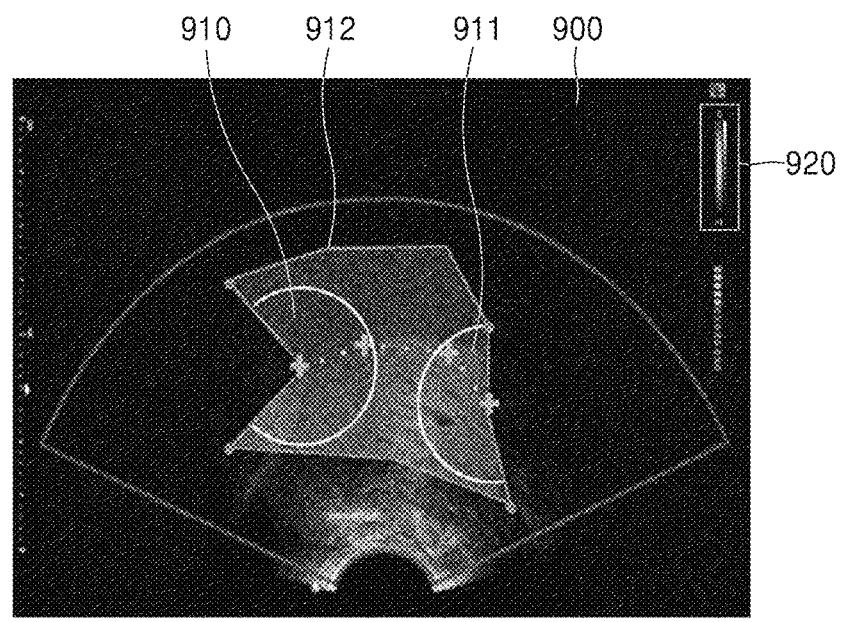
FIGS. 9A to 9C are images showing a process of displaying information indicating a degree of elasticity, according to another embodiment.
Figure 9B:
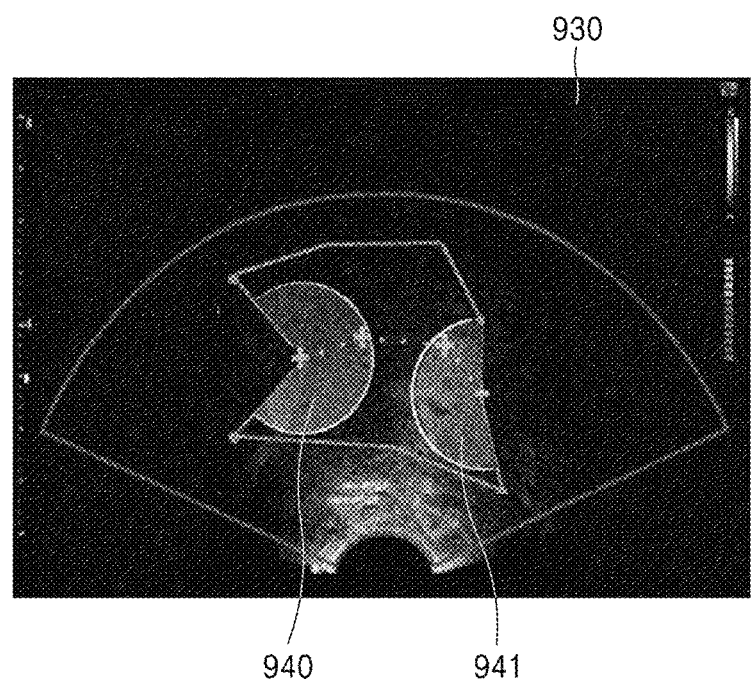
Figure 9C:
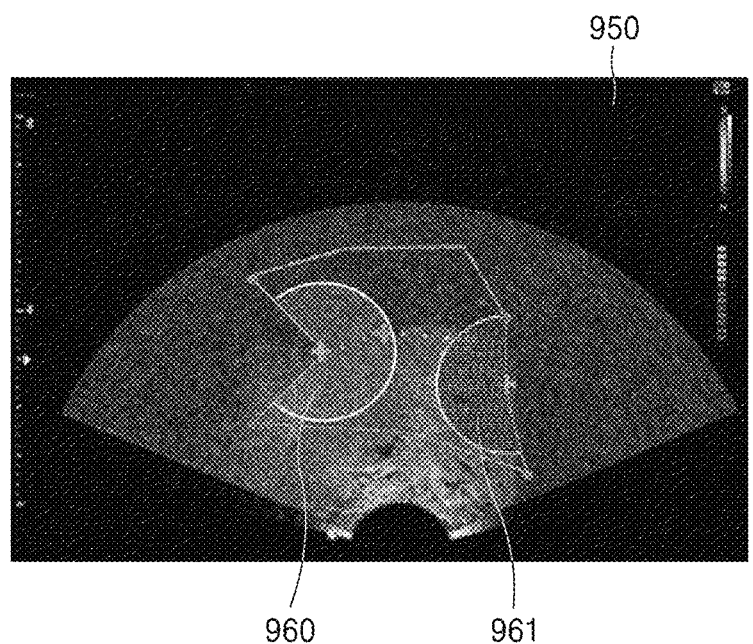

FIGS. 9A to 9C are images showing a process of displaying information indicating a degree of elasticity, according to another embodiment.

The ultrasound imaging apparatus 300 according to an embodiment may display information about a ROI of the IOS, a ROI of the EOS, and an ROI of the cervix to be overlapped on an ultrasonic image in an elastography image of an object.

Referring to FIG. 9A, as a ROI of the IOS 910 and a ROI of the EOS 911 are set and an ROI of the cervix 912 is determined, the ultrasound imaging apparatus 300 may display portions corresponding to the ROI of the IOS 910, the ROI of the EOS 911, and the ROI of the cervix 912 in an elastography image, to be overlapped on an ultrasonic image 900. In this state, the ultrasound imaging apparatus 300 may display an indicator indicating colors mapped according to an elasticity value. For example, referring to FIG. 9A, the ultrasound imaging apparatus 300 may display colors mapped according to the elasticity value, in form of a bar 920. Accordingly, the user may more easily determine a level of elasticity in each ROI, by referring to the displayed indicator.

The ultrasound imaging apparatus 300 according to an embodiment may display information about a selected ROI from among the ROI of the IOS, the ROI of the EOS, and the ROI of the cervix in the elastography image, to be overlapped on the ultrasonic image. For example, in order to determine the risk of premature birth, the user may check the degrees of elasticity only in the ROI of the IOS and the ROI of the EOS. In this state, the ultrasound imaging apparatus 300 may display information about the ROI of the IOS and the ROI of the EOS in the elastography image, to be overlapped on the ultrasonic image. Referring to FIG. 9B, the ultrasonic imaging apparatus 300 may display portions corresponding to a ROI of the IOS 940 and a ROI of the EOS 941 in the elastography image, to be overlapped on an ultrasonic image 930. Accordingly, the user may more easily compare the degrees of elasticity in the ROI of the IOS 940 and the ROI of the EOS 941.

The ultrasound imaging apparatus 300 according to an embodiment may calculate the representative value representing the degrees of elasticity in the ROI of the IOS and the ROI of the EOS, and display a preset color corresponding to the calculated representative value to be overlapped on the ultrasonic image or the elastography image. In this state, the ultrasound imaging apparatus 300 may determine a color corresponding to the amount of a representative value, according to the amount of the representative value, and display the ROI of the IOS and the ROI of the EOS in the determined color.

For example, as illustrated in FIG. 9C, when the representative value representing the degree of elasticity in a ROI of the IOS 960 is 0.61 and the representative value representing the degree of elasticity in a ROI of the EOS 961 is 0.78, the ultrasound imaging apparatus 300 may determine a color corresponding to a representative value of 0.61 and a color corresponding to a representative value of 0.78, respectively, to be red and blue. The ultrasound imaging apparatus 300 may display a red color to be overlapped over the ROI of the IOS 960 of an elastography image 950 and a blue color to be overlapped over the ROI of the EOS 961 of the elastography image 950. Accordingly, the user may more easily compare the degrees of elasticity in the ROI of the IOS 960 and the ROI of the EOS 961, through the difference in color displayed in the ROI of the IOS 960 and the ROI of the EOS 961.

Figure 10:
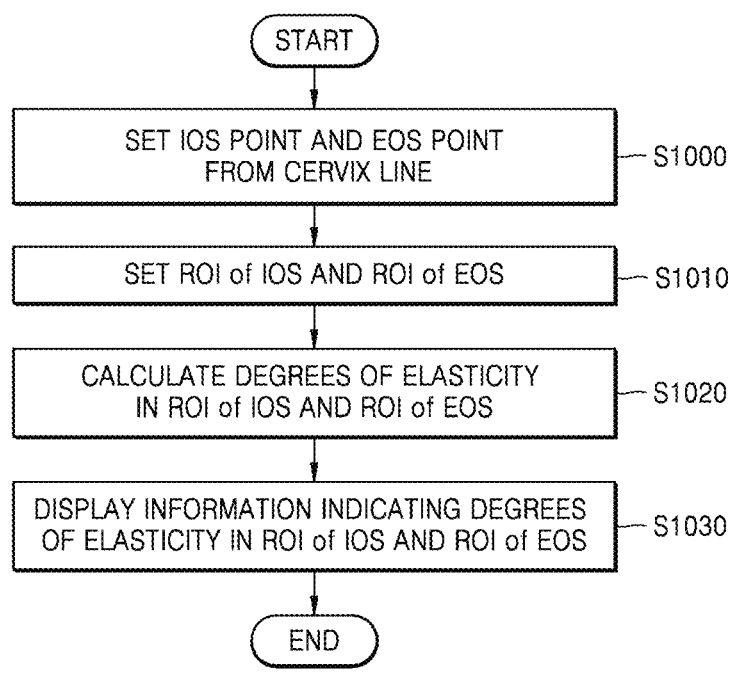
FIG. 10 is a flowchart for explaining an ultrasound image display method according to an embodiment.

FIG. 10 is a flowchart for explaining an ultrasound image display method according to an embodiment.

The respective operations of an ultrasound image display method may be performed by an ultrasound imaging apparatus including a processor capable of image processing and a storage medium. In the present specification, an embodiment in which the ultrasound imaging apparatus 300 according to the above embodiments performs the ultrasound image display method is mainly described. Accordingly, the embodiments described with respect to the ultrasound imaging apparatus 300 may be applied to the ultrasound image display method, and reversely, an embodiment to be described below with respect to the ultrasound image display method may be applied to the above-described embodiments of the ultrasound imaging apparatus 300. The ultrasound image display method according to the present embodiment is not limited to one being performed by the ultrasound imaging apparatus 300 according to the above embodiments, but may be performed by various types of ultrasound imaging apparatuses. Any redundant description presented for the ultrasound imaging apparatus 300 is omitted.

In S1000, the ultrasound imaging apparatus 300 according to an embodiment may set an IOS point and an EOS point from a cervix line.

In S1010, the ultrasound imaging apparatus 300 according to an embodiment may set a ROI of the IOS and a ROI of the EOS based on the IOS point and the EOS point.

To set the ROI of the IOS, the ultrasound imaging apparatus 300 may generate a first guide line and a second guide line, each having a start point at the IOS point. In order to more accurately set the ROI of the IOS, the ultrasound imaging apparatus 300 may receive an external input to adjust the positions of endpoints of the first guide line and the second guide line. The ultrasound imaging apparatus 300 may set the ROI of the IOS based on the endpoint of the first guide line and the endpoint of the second guide line, whose positions are adjusted, and the IOS point.

Furthermore, to set the ROI of the EOS, the ultrasound imaging apparatus 300 may generate a third guide line and a fourth guide line, each having a start point at the EOS point. In order to more accurately set the ROI of the EOS, the ultrasound imaging apparatus 300 may receive an external input to adjust the positions of endpoints of the third guide line and the fourth guide line. The ultrasound imaging apparatus 300 may set the ROI of the EOS based on the endpoint of the third guide line and the endpoint of the fourth guide line, whose positions are adjusted, and the EOS point. For example, the ultrasound imaging apparatus 300 may set the ROI of the IOS and the ROI of the EOS, respectively having a fan shape having the center of a circle at the IOS point and the EOS point.

Furthermore, the ultrasound imaging apparatus 300 according to an embodiment may set a ROI of the cervix including the set ROI of the IOS and ROI of the EOS. For example, the ultrasound imaging apparatus 300 may determine the ROI of the cervix based on the endpoints of the first guide line, the second guide line, the third guide line, and the fourth guide line, and the cervix line. For example, the ultrasound imaging apparatus 300 may connect the endpoint of the first guide line and the endpoint of the third guide line such that a line connecting the endpoint of the first guide line and the endpoint of the third guide line may have a form of the cervix line. Furthermore, the ultrasound imaging apparatus 300 may connect the endpoint of the second guide line and the endpoint of the fourth guide line such that a line connecting the endpoint of the second guide line and the endpoint of the fourth guide line may have a form of the cervix line. The ultrasound imaging apparatus 300 may determine the ROI of the cervix by connecting the endpoints of the first guide line, the second guide line, the third guide line, and the fourth guide line, and the IOS point and the EOS point.

In S1020, the ultrasound imaging apparatus 300 may calculate the degrees of elasticity in the ROI of the IOS and the ROI of the EOS.

For example, the ultrasound imaging apparatus 300 may extract information about the ROI of the IOS and the ROI of the EOS from an elastography image showing the same object as that in an ultrasonic image. According to another embodiment, the ultrasound imaging apparatus 300 may calculate a representative value representing the degree of elasticity in each of the ROI of the IOS and the ROI of the EOS. Furthermore, the ultrasound imaging apparatus 300 may calculate the cervical length based on the cervix line.

Furthermore, according to the present embodiment, the ultrasound imaging apparatus 300 may determine the risk of premature birth based on the degrees of elasticity in the ROI of the IOS and the ROI of the EOS, and the cervical length.

In S1030, the ultrasound imaging apparatus 300 may display information indicating the degrees of elasticity in the ROI of the IOS and the ROI of the EOS.

For example, the ultrasound imaging apparatus 300 may display information indicating the degrees of elasticity in the ROI of the IOS and the ROI of the EOS in a text form. According to another embodiment, the ultrasound imaging apparatus 300 may display information about the ROI of the IOS and the ROI of the EOS in the elastography image to be overlapped on the ultrasonic image. Furthermore, the ultrasound imaging apparatus 300 may display the cervical length with the information indicating the degrees of elasticity in the ROI of the IOS and the ROI of the EOS. Furthermore, the ultrasound imaging apparatus 300 may output a result of the determination of the risk of premature birth. For example, the ultrasound imaging apparatus 300 may display information indicating the risk of premature birth by a percentage or a certain value, but the present disclosure is not limited thereto.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:
1. An ultrasound imaging apparatus comprising:
a processor configured to:
set an internal orifice of a uterus (IOS) point and an external orifice of a uterus (EOS) point, from a cervix line indicating a cervical canal; and
a display configured to display a first guide line and a second guide line, each having a start point at the IOS point, and display a third guide line and a fourth guide line, each having a start point at the EOS point,
wherein the processor:
receives a user input for selecting a first point, a second point, a third point, and a fourth point,
adjusts a position of an endpoint of the first guide line to the first point and adjusts a position of an endpoint of the second guide line to the second point,
sets a region of interest (ROI) of the IOS, wherein a shape of the ROI of the IOS being a sector having a radius of a predetermined size, and a center angle of the ROI of the IOS being defined by the first guide line and the second guide line,
adjusts a position of an endpoint of the third guide line to the third point and adjusts a position of an endpoint of the fourth guide line to the fourth point,
sets a ROI of the EOS, wherein a shape of the ROI of the EOS being a sector having a radius of a prede- termined size, and a center angle of the ROI of the EOS being defined by the third guide line and the fourth guide line, and calculates degrees of elasticity in the ROI of the IOS and the ROI of the EOS, and wherein the display is configured to displays the ROI of the IOS, the ROI of the EOS, and information indicating the degrees of elasticity in the ROI of the IOS and the ROI of the EOS.

2. The ultrasound imaging apparatus of claim 1, wherein the processor sets a ROI of a cervix including the ROI of the IOS and the ROI of the EOS, and calculates a degree of elasticity in the ROI of the cervix, and the display displays information indicating the degree of elasticity in the ROI of the cervix.

3. The ultrasound imaging apparatus of claim 1, wherein the processor determines a ROI of a cervix based on the endpoint of the first guide line, the endpoint of the second guide line, the endpoint of the third guide line, and the endpoint of the fourth guide line, and the cervix line.

4. The ultrasound imaging apparatus of claim 3, wherein the processor determines the ROI of the cervix by connecting the endpoint of the first guide line, the endpoint of the second guide line, the endpoint of the third guide line, and the endpoint of the fourth guide line, the IOS point, and the EOS point, and a line connecting the endpoint of the first guide line and the endpoint of the third guide line and a line connecting the endpoint of the second guide line and the endpoint of the fourth guide line each have a shape of the cervix line.

5. The ultrasound imaging apparatus of claim 1, wherein the display displays information about the ROI of the IOS and the ROI of the EOS in an elastography image with respect to an object to be overlapped on an ultrasonic image.

6. The ultrasound imaging apparatus of claim 1, wherein the processor calculates a cervical length based on the cervix line, and the display displays the cervical length with the information indicating the degrees of elasticity in the ROI of the IOS and the ROI of the EOS.

7. The ultrasound imaging apparatus of claim 6, wherein the processor determines a risk of premature birth based on the degrees of elasticity in the ROI of the IOS and the ROI of the EOS, and the cervical length, and the display outputs a result of the determination of the risk of premature birth.

8. The ultrasound imaging apparatus of claim 1, further comprising a data acquirer including an ultrasound probe, configured to acquire ultrasound data about an object including a cervix, wherein the processor generates an ultrasonic image based on the acquired ultrasound data.

9. An ultrasound image display method comprising:

setting an internal orifice of a uterus (IOS) point and an external orifice of a uterus (EOS) point, from a cervix line indicating a cervical canal, displaying a first guide line and a second guide line, each having a start point at the IOS point, and displaying a third guide line and a fourth guide line, each having a start point at the EOS point, receiving a user input for selecting a first point, a second point, a third point and a fourth point, adjusting a position of an endpoint of the first guide line to the first point and adjusting a position of an endpoint of the second guide line to the second point, setting a region of interest (ROI) of the IOS, wherein a shape of the ROI of the IOS being a sector having a radius of a predetermined size, and a center angle of the ROI of the IOS being defined by the first guide line and the second guide line, adjusting a position of an endpoint of the third guide line to the third point and adjusting a position of an endpoint of the fourth guide line to the fourth point, setting a ROI of the EOS, wherein a shape of the ROI of the EOS being a sector having a radius of a predetermined size, and a center angle of the ROI of the EOS being defined by the third guide line and the fourth guide line, calculating degrees of elasticity in the ROI of the IOS and the ROI of the EOS; and displaying the ROI of the IOS, the ROI of the EOS, and information indicating the degrees of elasticity in the ROI of the IOS and the ROI of the EOS.

10. The ultrasound image display method of claim 9, further comprising:

setting a ROI of a cervix including the ROI of the IOS and the ROI of the EOS;

calculating a degree of elasticity in the ROI of the cervix; and displaying information indicating the degree of elasticity in the ROI of the cervix.

11. The ultrasound image display method of claim 9, further comprising determining a ROI of a cervix based on the endpoint of the first guide line, the endpoint of the second guide line, the endpoint of the third guide line, and the endpoint of the fourth guide line, and the cervix line.

12. The ultrasound image display method of claim 11, wherein the determining of the ROI of the cervix comprises determining the ROI of the cervix by connecting the endpoint of the first guide line, the endpoint of the second guide line, the endpoint of the third guide line, and the endpoint of the fourth guide line, the IOS point, and the EOS point, and a line connecting the endpoint of the first guide line and the endpoint of the third guide line and a line connecting the endpoint of the second guide line and the endpoint of the fourth guide line each have a shape of the cervix line.

13. The ultrasound image display method of claim 9, wherein the displaying of the information indicating the degrees of elasticity in the ROI of the IOS and the ROI of the EOS comprises displaying information about the ROI of the IOS and the ROI of the EOS in an elastography image with respect to an object to be overlapped on an ultrasonic image.

14. The ultrasound image display method of claim 9, further comprising:

calculating a cervical length based on the cervix line;

determining a risk of premature birth based on the degrees of elasticity in the ROI of the IOS and the ROI of the EOS, and the cervical length; and outputting a result of the determination of the risk of premature birth.

15. A non-transitory computer readable storage medium having stored thereon a program, which when executed by a computer, performs an ultrasound image display method, the ultrasound image display method comprising:

setting an internal orifice of a uterus (IOS) point and an external orifice of a uterus (EOS) point, from a cervix line indicating a cervical canal, displaying a first guide line and a second guide line, each having a start point at the IOS point, and displaying a third guide line and a fourth guide line, each having a start point at the EOS point, receiving a user input for selecting a first point, a second point, a third point and a fourth point, adjusting a position of an endpoint of the first guide line to the first point and adjusting a position of an endpoint of the second guide line to the second point, setting a region of interest (ROI) of the IOS wherein a shape of the ROI of the IOS being a sector having a radius of a predetermined size, and a center angle of the ROI of the IOS being defined by the first guide line and the second guide line, adjusting a position of an endpoint of the third guide line to the third point and adjusting a position of an endpoint of the fourth guide line to the fourth point, setting a ROI of the EOS, wherein a shape of the ROI of the EOS being a sector having a radius of a predetermined size, and a center angle of the ROI of the EOS being defined by the third guide line and the fourth guide line, calculating degrees of elasticity in the ROI of the IOS and the ROI of the EOS; and displaying the ROI of the IOS, the ROI of the EOS, and information indicating the degrees of elasticity in the ROI of the IOS and the ROI of the EOS.

* * * * *